(12) United States Patent
Hubbard-Nelson et al.

(10) Patent No.: US 7,440,541 B2
(45) Date of Patent: Oct. 21, 2008

(54) DUAL SOURCE XRF SYSTEM

(75) Inventors: Bradley Hubbard-Nelson, Concord, MA (US); Peter John Hardman, Woburn, MA (US)

(73) Assignee: Innov-X-Systems, Inc., Woburn, MA (US)

( * ) Notice: Subject to any disclaimer, the term of this patent is extended or adjusted under 35 U.S.C. 154(b) by 39 days.

(21) Appl. No.: 11/645,907

(22) Filed: Dec. 27, 2006

(65) Prior Publication Data
US 2008/0159474 A1    Jul. 3, 2008

(51) Int. Cl.
*G01N 23/223* (2006.01)
(52) U.S. Cl. .......................................... 378/45; 378/47
(58) Field of Classification Search .............. 378/44–50
See application file for complete search history.

(56) References Cited

U.S. PATENT DOCUMENTS

| | | | |
|---|---|---|---|
| 4,599,741 A | | 7/1986 | Wittry |
| 5,657,363 A | * | 8/1997 | Hossain et al. ................ 378/45 |
| 6,859,517 B2 | | 2/2005 | Wilson et al. |
| 7,099,433 B2 | | 8/2006 | Sommer et al. |
| 2007/0030953 A1 | | 2/2007 | Sommer et al. |

FOREIGN PATENT DOCUMENTS

JP    01156646 A    *    6/1989

* cited by examiner

*Primary Examiner*—Hoon Song
(74) *Attorney, Agent, or Firm*—Iandiorio Teska & Coleman

(57) ABSTRACT

A dual source tube XRF system and method wherein a first x-ray source is employed to direct x-rays in a first energy band at a sample and at least a second x-ray source is employed to direct x-rays in a second energy band at the sample. A detector is responsive to x-rays emitted by the sample after irradiation by the first and second x-ray sources. An analyzer is responsive to the detector and is configured to determine the amount of at least a first substance in the sample based on irradiation of the sample by the first x-ray source and to determine the amount of at least a second substance in the sample based on irradiation of the sample by the second x-ray source. A controller is responsive to the analyzer and is configured to energize the first and second x-ray sources either simultaneously or sequentially.

15 Claims, 5 Drawing Sheets

S: 1%   Ca: .1%   V: .01%
Cr: 1%   Fe: .8%   Ni: .1%
Cu: .05%   Zr: .05%   Pb: 1%

Catalyst Fines

Na: .001%   Mg: .002%   Si: .01%
P: .01%   Al: .01%

DUAL SOURCE XRF SYSTEM

FIELD OF THE INVENTION

This subject invention relates to x-ray fluorescence (XRF) techniques and systems and, in one particular example, to an XRF system and method used to analyze fuels, oils, and additives.

BACKGROUND OF THE INVENTION

X-ray fluorescence (XRF) is a technique used to measure the elemental composition of a sample. The sample is excited by a source of x-rays, and emits its own characteristic x-rays. A detector is responsive to the x-rays emitted from the sample. An analyzer processes the output signals produced by the detector and divides the energy levels of the detected x-ray photons into energy subranges by counts of the number of x-ray photons detected to produce a graph depicting the x-ray spectrum of the sample.

In XRF, the sample is irradiated with x-rays either from a radioactive isotope source or, more commonly, from an x-ray tube. A typical isotope source, for example Fe-55, has a limited range of emitted x-ray energies which cannot be changed. Therefore to excite a wide range of elements efficiently, the use of multiple sources is required. See U.S. Pat. No. 6,859,517 incorporated herein by this reference. In systems where an x-ray tube is used to provide the exciting radiation, it is often sufficient to use only a single x-ray tube because the x-ray energy distribution can be changed by controlling the high voltage supply and by applying filters between the source and sample. The output of an x-ray tube is composed of discrete lines, which are specific to the anode material of the tube, superimposed onto a continuum background of energies which extend up to the maximum energy of the supplied high voltage. By changing the anode material of the tube, it is possible to select characteristic lines at different energies thus avoiding potential overlaps between elemental lines from the anode and those in the sample, or to choose a line which can efficiently excite a particular element in the sample.

A general purpose XRF system typically employs a single x-ray tube equipped with high voltage control and uses a range of different filters to provide an instrument which can be applied to a whole range of different analytical problems. It is possible to enhance the performance of an instrument for a specific application by changing the tube anode material to produce characteristic lines which more efficiently excite the element(s) of interest. When the range of elements to be analyzed is limited, it is also possible to create a monochromatic x-ray beam which can give exceptional sensitivity for the chosen elements. An example is the analysis of low concentrations of sulfur (<1 ppm) in diesel fuel. Because diesel fuel is a well-known hydrocarbon mixture with a well defined chemistry, may be no need to measure any other elements besides sulfur in these samples. The effects of the hydrocarbon matrix are included in the calibration method. The matrix does not change appreciably for different samples and there are no other elements of appreciable concentration (besides the base hydrocarbon elements C, H, O) thus there may be no need to measure other elements besides sulfur.

A general problem in XRF analysis is the need to analyze a wide range of elements in a sample whereby high concentrations of some elements mask the presence of, or interfere with, low concentrations of other elements that also must be measured. A high concentration of an element can produce a large response in the measured energy spectrum. The large peak in the spectrum generates excessive background in the detector that reduces the signal-to-background ratio of other elements. The ideal case is to measure the sample with one source configuration where the higher concentration elements are measured, and then measure the sample with a different source where the high concentration elements are not excited by that source thus minimizing the background in the spectral region of the other elements of interest. There are numerous examples of this general problem. For example, in environmental soil samples it is desirable to measure low concentrations (<50 ppm) of Cr in soil. Often, however, iron concentrations in soil exceed several percent. In an XRF spectrum, the iron peak is centered at 6.4 keV and the Cr peak is centered at 5.4 keV. The state of the art in small semiconductor detectors typically used in commercial devices have a relatively high iron peak that produces a background "tail" into the chromium region. This background tail obscures the low concentrations of chromium that need to be measured.

Recently, there is also a need to analyze lubricant and fuel oil samples for the presence of S, Cr, V, Fe, Ni, Cu, Zn and other elements. These elements are either naturally occurring in the fuels and oils or are present as additives or contaminants (wear metals). There is also a need to analyze fuel samples for the presence of catalysts fines (catfines), typically, silicon, and aluminum. In an XRF system with a single x-ray tube, the spectrum would be dominated by the high levels (0.5-5.0%) of sulfur in the sample which makes the analysis of low levels (<80 ppm) of aluminum and silicon extremely difficult if not impossible. In spectrum from a standard XRF measurement, a high sulfur peak is seen in the region around the x-axis value of 2,300 eV. The area of interest for aluminum and silicon is approximately 1,500 and 1,750 eV respectively. The background "tailing" from the high sulfur concentration extends down to past the lower region of the spectrum where Al and Si are to be measured. The only way to achieve the required sensitivity for Al and Si (<80 ppm detection limit) is to produce an x-ray spectrum that eliminates the high sulfur peak.

One practical method of analyzing the small amounts of aluminum and silicon in samples containing high levels of sulfur is to use a low energy source of x-rays which does not excite the sulfur atoms. A simple approach would be to operate the x-ray tube at a voltage below the absorption edge of sulfur 2.472 keV but this approach would yield an extremely small number of useful x-rays from the source. A more efficient solution is to operate a molybdenum anode tube at a typical operating voltage e.g. 25 keV, and then monochromate the output beam to include only the Mo-L lines at 2.29 keV. The use of a monochromatic source to measure the catfines is discussed in co-pending U.S. application Ser. No. 11/585,367. The more general use of a monochromator to produce a mono-energetic beam of x-rays on a sample via a curved crystal is presented in U.S. Pat. No. 4,599,741 (Wittry et al.). Wittry et al describe a curved crystal structure combined with an x-ray source to produce a mono-energetic beam that would be effective for various XRF analysis applications. This patent does not specifically discuss the need to measure multiple elements sequentially, with multiple sources. Nor does it address the specific problem solved by our invention namely the ability to measure low concentrations of one group of elements in the presence of high concentrations of other elements that may interfering with the first measurement. For an instrument to be capable of measuring all the elements required in fuel oils and lubricants, it needs to combine the capabilities of standard tube excitation and also monochromatic excitation. In some configurations and applications, this could possibly be achieved by using a single x-ray tube to excite the sample, directly or via a monochromatic pathway, and could employ some mechanical devices to switch between one mode and another. However, for the situation where one of the elements to be measured by a direct beam is sulfur, and the elements to be measured by the monochromatic beam are aluminum and silicon, it is not possible to use the same tube anode material. This is because the Mo-L line (2.29 keV) lies at almost the same energy as S (2.307 keV), which means that it would not be possible to quantify the amount of sulfur in a sample. Finally, an accurate determination of the amount of aluminum and silicon in a sample depends on knowing the amount of sulfur and other elements in a sample. Therefore, it is important to quantify all elements in a material using the same instrument, so that results from multiple measurements can be combined into a final result.

A scientist using a laboratory based XRF system may be able to adjust their determinations when analyzing a sample based on the scientist's advanced knowledge of chemistry, physics, and the specifications of the XRF system used. But, a fuel sample would typically be analyzed in the field often by less knowledgeable technicians.

SUMMARY OF THE INVENTION

It is therefore an object of this invention to provide a more automated XRF system.

It is a further object of this invention to provide such an automated XRF system which, in one example, is able to determine the concentration of both lower atomic number elements and higher atomic number elements.

It is a further object of this invention to provide such an automated XRF system which, in one example, is able to determine the concentration of both sulfur and also the concentration of catfines in a fuel sample.

It is a further object of this invention to provide such an automated XRF system which, in one example, automatically takes into account the concentration of sulfur when determining the concentration of aluminum in a fuel sample.

It is a further object of this invention to provide a more advanced method of analyzing a sample using x-rays.

It is a further object of this invention to provide such an XRF system which is more robust, easy to use, and ergonomic in design.

The subject invention results from the realization that by incorporating at least two x-ray sources in an XRF system, the concentration of different elements in a sample can be more reliably determined and, moreover, the concentration of one element based on irradiation of the sample by one x-ray source can be taken into account when determining the concentration of another element after irradiation of the sample by the other x-ray source. A dual tube system is effected whereby a sample is automatically measured sequentially by the first source, then the second source, and the results from the first source measurement are used to automatically correct the results from the second source. Moreover, one or both sources are tuned so that they optimally excite one group of elements but minimally excite the other group of elements. Since high concentrations of one or more elements in the sample may interfere with the measurements of other elements in the sample, the subject invention overcomes certain limitations associated with the prior art. In one embodiment, either or both sources may be used in combination with a monochromator to produce a quasi mono-energetic x-ray source.

The subject invention, however, in other embodiments, need not achieve all these objectives and the claims hereof should not be limited to structures or methods capable of achieving these objectives.

The subject invention features a dual source XRF system. A first x-ray source directs x-rays in a first energy band at a sample. The first x-ray source is chosen to not excite a high concentration element in the sample. A second x-ray source directs x-rays in a second energy band at the sample. The second x-ray source is chosen to excite the high concentration element. A monochromator is in the optical path between the first and/or second x-ray source and the sample. A detector is responsive to x-rays emitted by the sample after irradiation by the first and second x-ray sources. An analyzer is responsive to the detector and is configured to detect a low concentration in the sample based on irradiation of the sample by the first x-ray source and to detect at least the high concentration element in the sample based on irradiation of the sample by the second x-ray source and to determine the amount of the high and low concentration elements. The determination of the low concentration element in the sample is based on the determined amount of the high concentration element in the sample.

One dual source XRF system in accordance with the subject invention features a first x-ray source for directing x-rays in a first energy band at a sample and at least a second x-ray source for directing x-rays in a second energy band at the sample. A detector is responsive to x-rays emitted by the sample after irradiation by the first and second x-ray sources. An analyzer is responsive to the detector and is configured to detect and typically determine the amount of at least a first substance in the sample based on irradiation of the sample by the first x-ray source and to detect and typically determine the amount of at least a second substance in the sample based on irradiation of the sample by the second x-ray source. A controller, responsive to the analyzer, is configured to energize the first and second x-ray sources either simultaneously or sequentially. Preferably, the analyzer adjusts the determination of the second substance in the sample based on the determined amount of the first substance in the sample.

In one specific example, first x-ray source is a silver anode x-ray tube and the second x-ray source is a molybdenum anode x-ray tube. Preferably, a monochromator is placed in the optical path between the molybdenum anode x-ray tube and the sample. One preferred monochromator includes doubly curved optics.

When the sample is fuel oil, the analyzer can be configured to determine the amount of sulfur in the fuel oil sample based on irradiation of the fuel sample by the first x-ray source. The analyzer is also configured to determine the amount of catalyst fines in the fuel oil sample based on irradiation of the fuel sample by the molybdenum anode x-ray tube. Furthermore, if the determination of the amount of aluminum in the fuel oil sample depends on the amount of sulfur in the sample, the analyzer can be configured to adjust the determination depending on the determined amount of sulfur in the sample. One method of analyzing a sample, in accordance with this invention, includes energizing a first x-ray source to direct x-rays in a first energy band at a sample and energizing at least a second x-ray source to direct x-rays in a second energy band at the sample. X-rays emitted by the sample are detected. The amount of at least a first substance in the sample is determined based on irradiation of the sample by the first x-ray source and the amount of at least a second substance in the sample is determined based on irradiation of the sample by the second x-ray source. Further included may be the step of adjusting the determination of the amount of the second substance in the sample based on the determined amount of the first substance in the sample.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Figure 1:
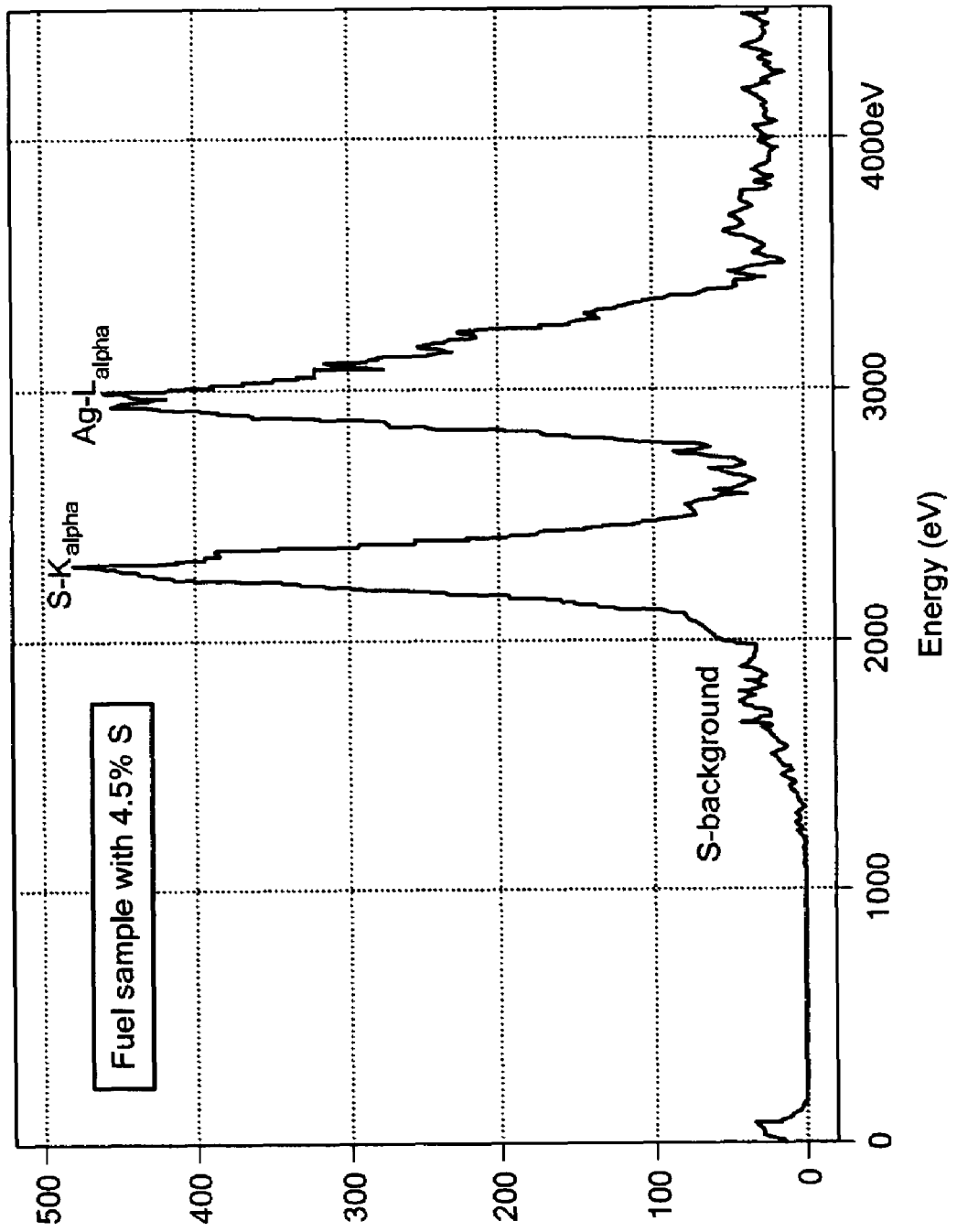
FIG. 1 is a graph depicting the x-ray spectrum of a typical fuel oil sample.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

FIG. 1 shows a spectrum from a standard XRF measurement. A high sulfur peak is seen in the region around the x-axis value of 2,300 eV. The area of interest for aluminum and silicon is approximately 1,500 and 1,750 eV respectively. The background "tailing" from the high sulfur concentration extends down to past the lower region of the spectrum where Al and Si are to be measured. The only way to achieve the required sensitivity for Al and Si (<80 ppm detection limit) is to produce an x-ray spectrum that eliminates the high sulfur peak.

Figure 2:
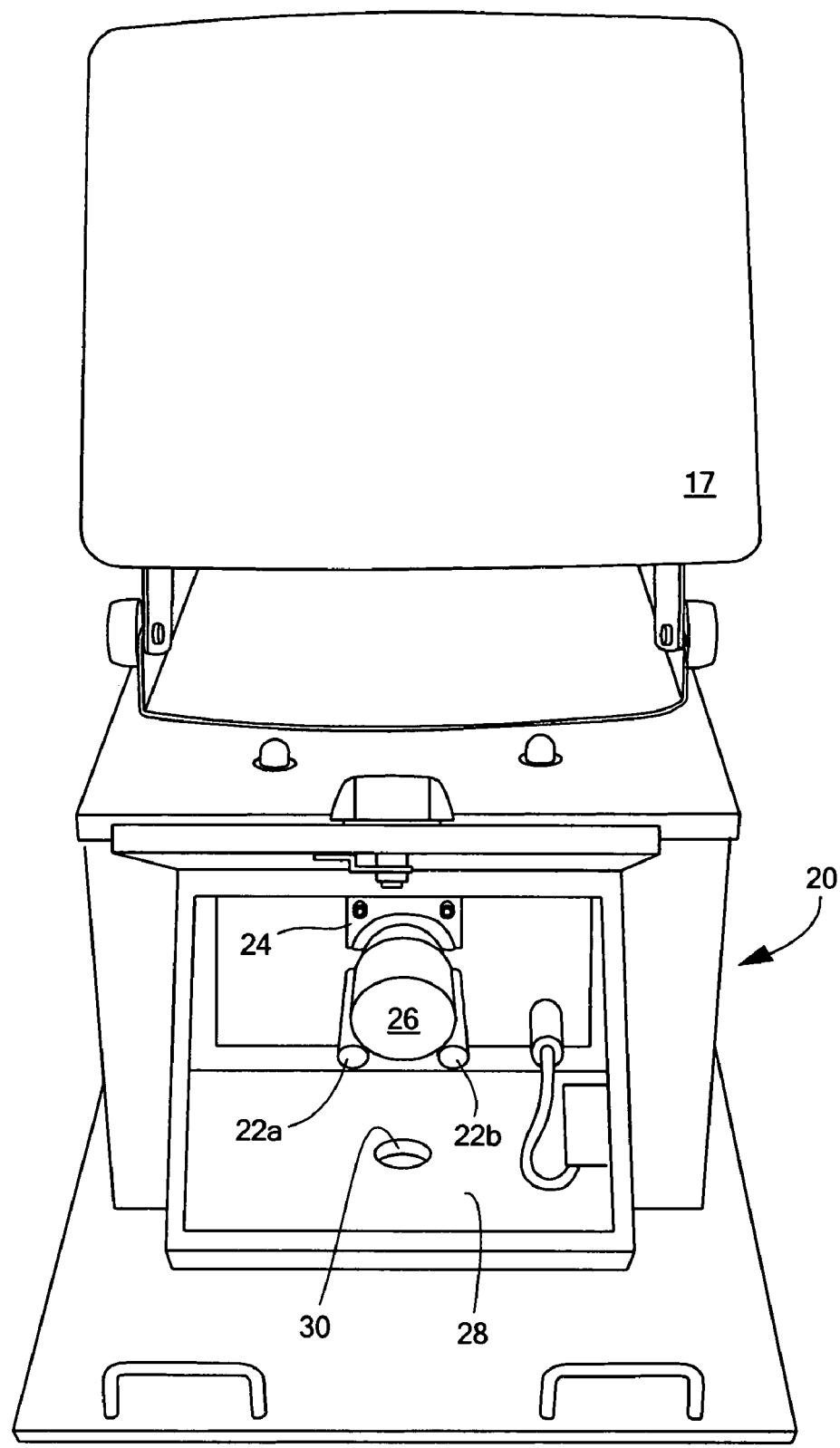
FIG. 2 is a schematic three-dimensional view showing an example of an XRF analyzer in accordance with the subject invention.

In one example, XRF system 20, FIG. 2, in accordance with the subject invention includes a sample bottle holder including posts 22a and 22b and sample bottle adapter 24 which positions novel sample bottle 26 horizontally with respect to unit 20. Should spillage occur, gravity will force the sample to flow down onto tray 28 with gravity drain 30. In this way, the electronic components within unit 20 will not be contaminated by inadvertent spills of the sample. See U.S. patent application Ser. No. 11/582,038 filed Oct. 17, 2006 by the same inventive entity hereof incorporated herein by this reference. Typically, a readout of the elements present in a sample within bottle 26 after analysis is displayed on display screen 17.

Figure 3:
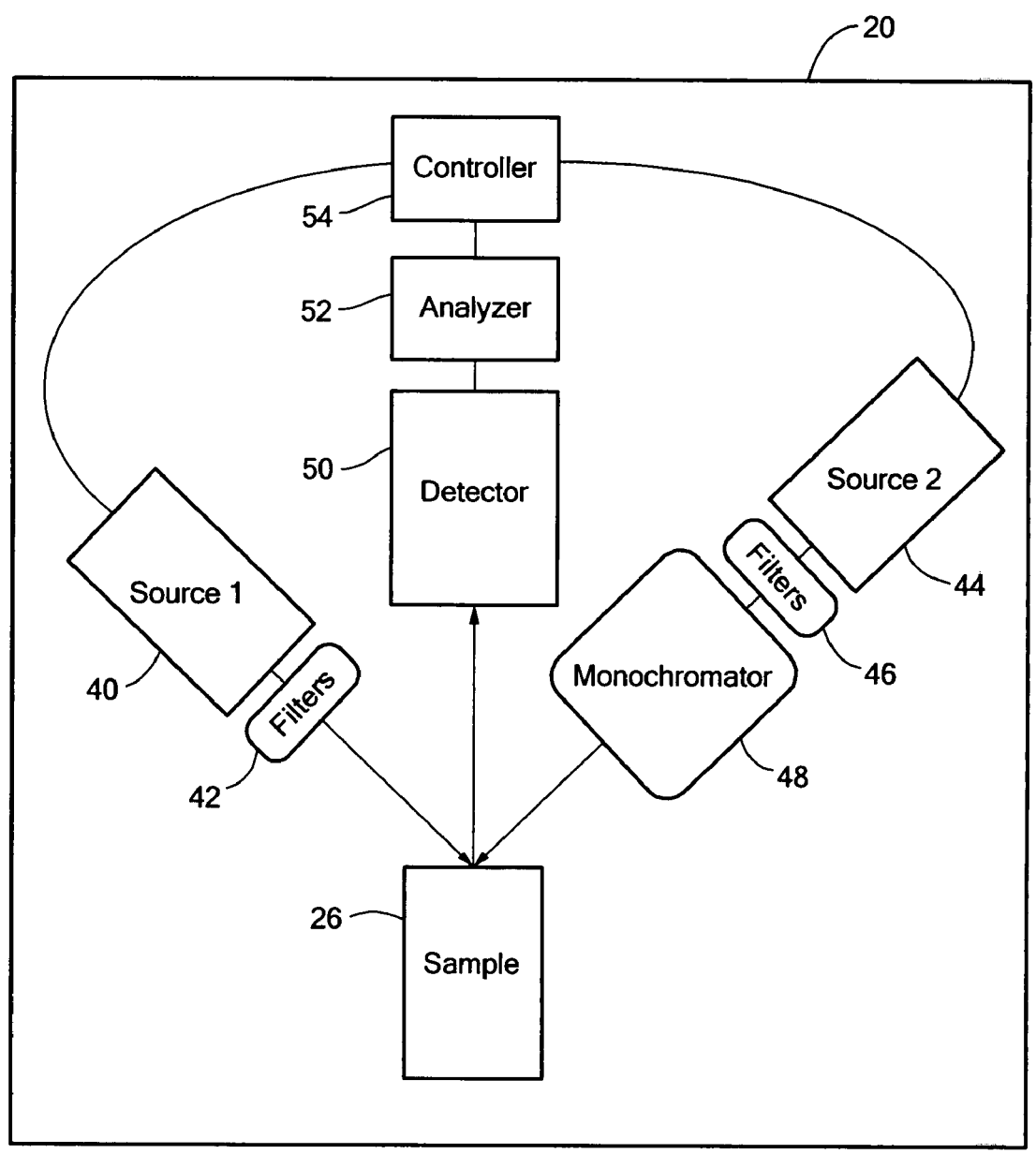
FIG. 3 is a block diagram showing the primary components associated with the XRF analyzer shown in FIG. 1.
Figures 4, 5:
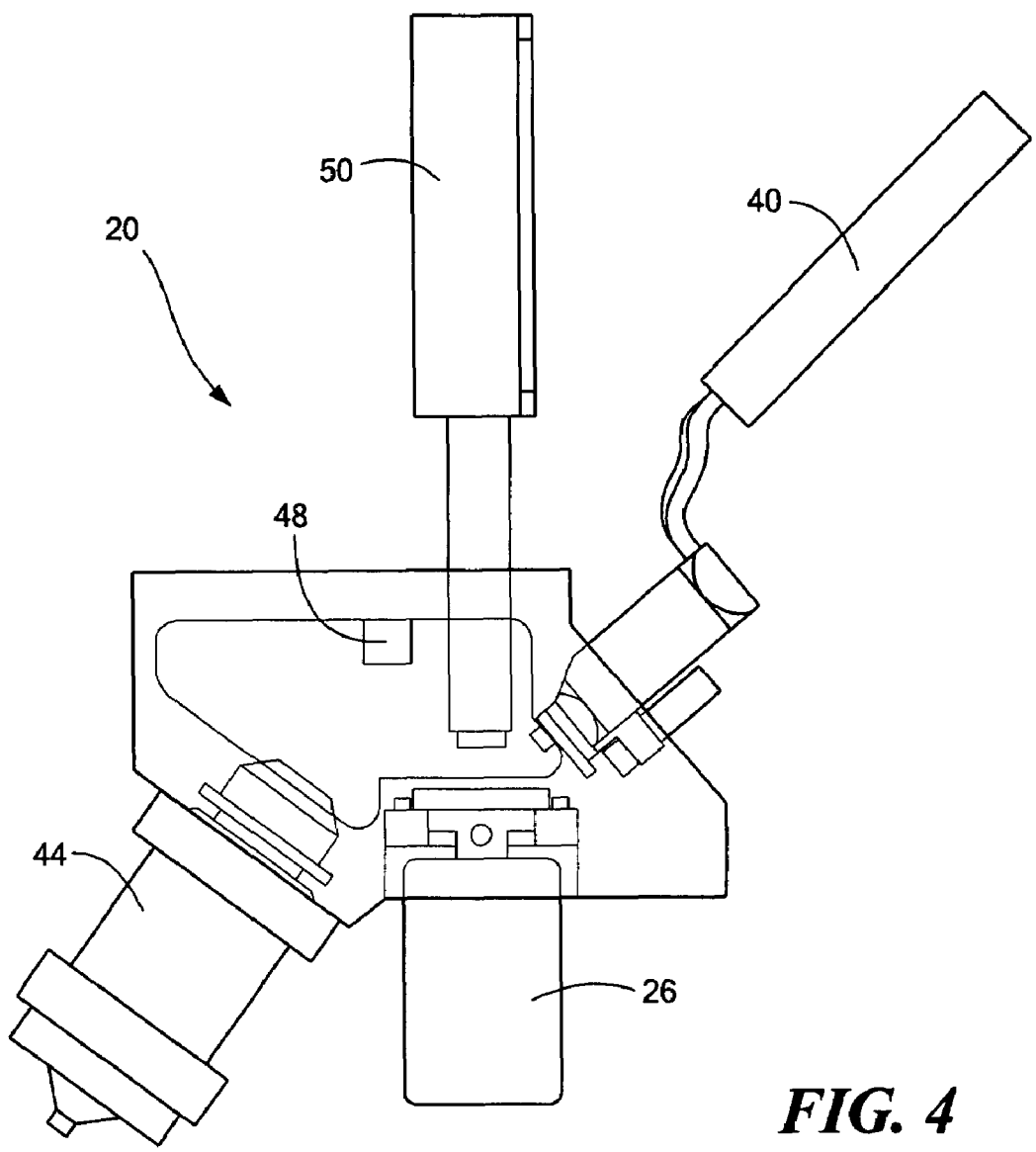
FIG. 4 is a schematic conceptual view of an XRF analyzer in accordance with the subject invention.
FIG. 5 is a schematic front view showing an example of a readout on the display of the XRF analyzer shown in FIG. 1.

System 20, FIGS. 3-4, in one preferred embodiment, includes x-ray source 40 with optional filter or filters 42 for directing x-rays in a first energy band at a sample in bottle 26. 1 mm Al filter at 25 kV and a 5 um Ag filter at 12 kV may be used. X-ray source 40 may be a silver anode x-ray tube. System 20 also includes x-ray source 44 with optional filter or filters 46 for directing x-rays in a second energy band at sample 26. X-ray source 44 may be a molybdenum anode x-ray tube. A monochromator 48 is preferably located in the optical path between x-ray source 44 and sample bottle 26. Molybdenum anode x-ray tube 44 emits x-rays at an energy level (2.293 keV) below but proximate the absorption edge of sulfur (2.472 keV). Monochromator 48 directs x-rays at a single energy level to the sample to limit excitation of any sulfur in the fuel sample. Monochromator 48 may comprise doubly curved crystal optics (X-Ray Optical Systems, Inc., East Greenbush, N.Y.), a doubly curved HOPG, (Optigraph GmbH DE, GE Advanced Materials, U.S.), or a multilayer optic (Osmic, Auburn Hills Mich.), or another equivalent device.

In another example, for the examination of low levels of S and P in steels, x-ray tube 44 is a silver anode source. Monochromator 48 produces mono-energetic Ag-L radiation (2.984 keV) which excites sulfur and phosphorus but avoids excitation of Cr and Fe. The second x-ray source 40 is used to measure other elements such as Cr and Fe. This embodiment would be used when it is also desired to measure low levels of sulfur in fuel, since the Ag L-line x-rays are ideal for excitation of S. Other x-ray sources include palladium and rhodium anode sources.

Detector 50 is responsive to x-rays emitted by sample 26 whether irradiated by x-ray sources 40 or 44. Analyzer 52 is responsive to detector 50 and is configured (e.g., programmed) to detect and typically determine the amount of elements in the sample based on irradiation of the sample by first x-ray source 40 and to detect and typically determine the amount of a additional elements in the sample based on irradiation of the sample by second x-ray source 44.

In this way, when the sample is fuel, the x-ray source 40, FIG. 3 is tailored to determine and display on display 17, FIG. 5 the amount or concentration of higher atomic number elements in the fuel such as sulfur, calcium, vanadium, iron, nickel, copper, zinc, and lead. The second x-ray source 44 in combination with monochromator 48 is tailored to determine and display on display 17, FIG. 5, the amount of lower atomic number elements such as sodium, magnesium, phosphorus, aluminum and silicon present in the fuel sample. Typically, controller 54 energizes or otherwise controls, typically sequentially, x-ray tubes 40 and 44. In one example, silver anode x-ray tube 40 is energized and analyzer 52 then performs an analysis of the sample. As is known in the art, x-ray photons detected by detector 50 are divided by analyzer 52 into several energy subranges by counts of the number of x-ray photons detected to analyze the x-ray spectrum of the sample. Thereafter, controller 54 turns off silver anode x-ray tube 40 and energizes or otherwise controls molybdenum anode tube 44 and then analyzer 52 again performs an analysis of a sample. For some embodiments of this invention, it could be possible to measure the sample with both beams simultaneously if the elements of interest are far enough apart to not interfere, and also at low enough concentrations.

Controller 54 and analyzer 52 may comprise separate circuitry, the circuitry of controller 52 and analyzer 52 may be combined in a single unit, or they may share circuitry and processing power.

Figure 6:
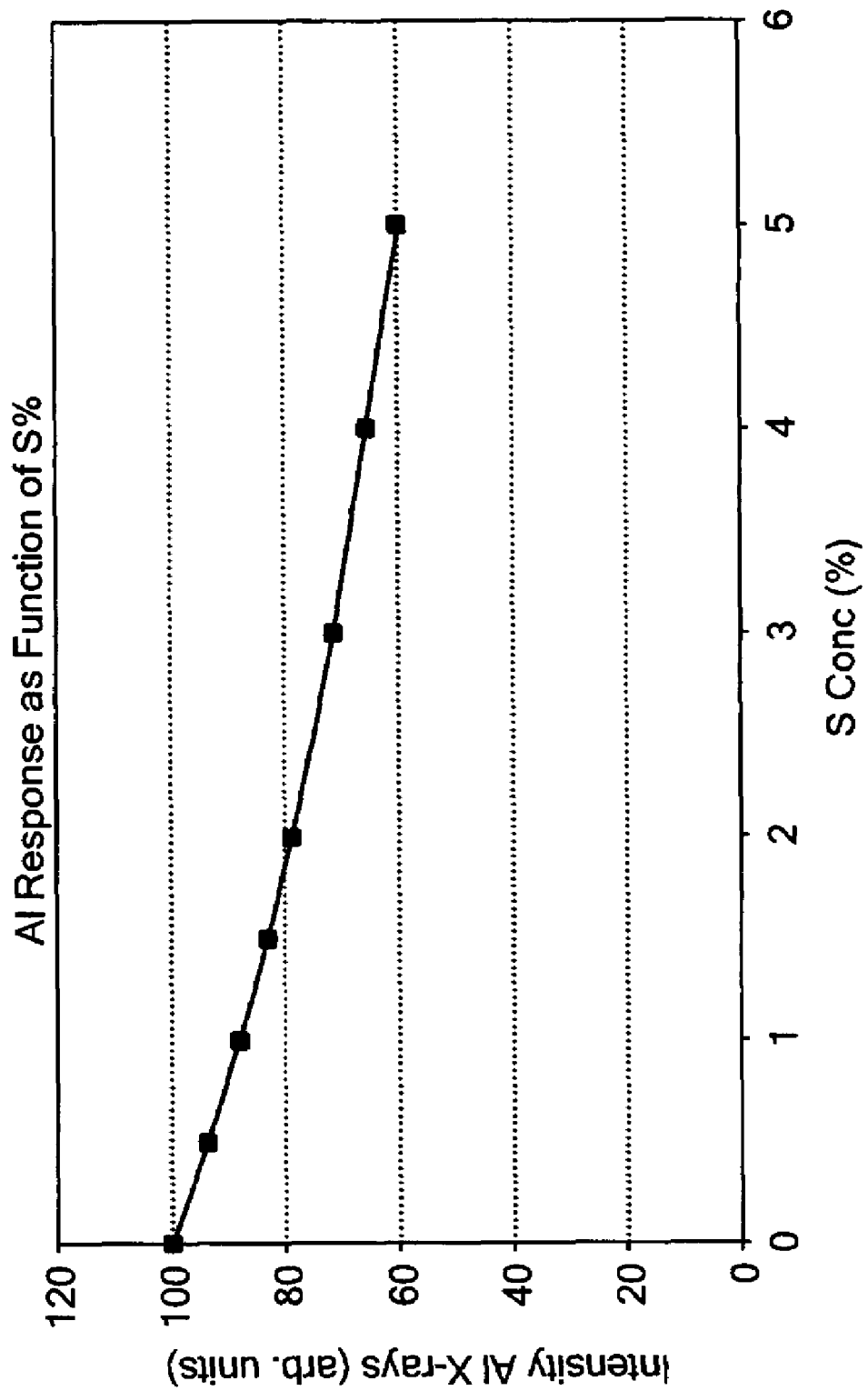
FIG. 6 is a graph depicting how the determination of the amount of aluminum in a fuel sample depends on the concentration of sulfur in the fuel sample.

In a further refinement, FIG. 6 depicts how the determination of the concentration of one element sometimes depends on the concentration of another element. In this example, the response (and thus the calibration) of the analyzer to Al or Si depends upon the concentration of sulfur in the sample. The sulfur concentration is unknown a priori and thus must be measured. FIG. 6 shows the effect of the response to Al as a function of sulfur concentration. Thus the analyzer measures the sulfur concentration, then measures the Al and Si response, then uses the sulfur concentration to correct the Al and Si response, then applies an algorithm and calibration data to convert the Al and Si response to concentration results. So, the analyzer of the subject invention can be uniquely programmed to adjust the determination of one substance in a sample based on the determined amount of another substance in the sample. In this example the response of the system for aluminum is different based upon the concentration of S in the sample. In order to accurately determine Al concentration in the sample, the S concentration must be measured as well, in order to correct for the effects on the Al response. Based on the measured result for S, the analyzer is configured to automatically adjusts the response to Al to produce an accurate measurement for Al (and for Si). Preferably, the analyzer does this automatically because typical operators are not always highly trained technical personnel.

In this way, when x-ray source 40, FIG. 3 is energized first to determine the concentration of sulfur in the sample, that concentration is stored and used to more accurately determine the concentration of aluminum in the sample when x-ray source 44 is energized. When the sulfur concentration is 1%, for example, the aluminum intensity is $I_2$. But, when the sulfur concentration is 0%, the aluminum intensity is $I_1$. In order for the analyzer to correctly convert the aluminum response to an accurate concentration C, it must measure the aluminum response, use the measured sulfur concentration and make a correction for the effect of sulfur concentration on the response, and then apply the appropriate calibration data to convert the aluminum response to an aluminum concentration. The same procedure is performed for silicon.

Thus, the subject invention has a particular use in the field of analyzing fuel samples. But, for other fields of use, those skilled in the art will understand how to select the appropriate types of x-ray sources (typically two or more) to be incorporated in an XRF analyzer in order to meet their specific needs. By incorporating at least two x-ray sources in an XRF system, the concentration of different substances including elements in a sample can be more reliably determined. In addition, the concentration of one substance can be taken into account to then more reliably determine the amount of another substance.

In one aspect, the invention is unique in that it uses at least two sources where one source is optimized for one range of elements including one or more high concentration elements (Group 1 elements). The second source is optimized for measuring low concentrations of additional elements (Group 2 elements), and in addition is specifically tuned to not excite high concentrations present in the sample that may interfere with the ability to measure Group 1 elements. The second source may be tuned by many methods. One preferred embodiment is the use of an x-ray tube and choice of anode material and optic that produces a monochromatic beam. The choice of optic shape and anode material is determined such that it creates a quasi mono-energetic x-ray source that is optimal for exciting Group 2 elements but does not excite Group 1 elements. With two sources, one or both sources use a choice of anode and optic for producing x-ray beams. The x-ray beams are used to sequentially irradiate a single sample. The results from the irradiation of the first source are used to quantify one group (i.e. Group 1) of elements. The irradiation by the second source is designed to optimally excite Group 2 elements, and to not excite high concentrations of one or more Group 1 elements. The spectral information from the first source and resulting concentration data is also used to automatically correct the results from the measurements of the Group 2 elements.

There are prior examples involving the uses of two irradiation sources but none to date use a combination of two sources to improve analytical capability as described above. Lab and portable XRF instruments have used two or more sources (typically isotopes) to sequentially irradiate samples. Examples include Niton's portable XRF, TN Technologies portable XRF, and laboratory instruments from Oxford and Asoma Instruments. In these systems, sources were chosen that were optimal for exciting two groups of elements. And, the results from the first source are also used to correct the results for the elements measured with the second source. However, there is no tuning of either source specifically to avoid excitation of certain high concentration elements. Two common sources in this case are Cd-109 and Fe-55 isotopes. For the marine example described above, the Fe-55 isotope emits an x-ray at 5.95 keV that could excite Si and Al (cat-fines) but would also efficiently excite sulfur in the sample.

Some portable and laboratory systems using x-ray tubes also will use a single tube, but with two sequential measurements to analyze a wider band of elements. In these cases, a single x-ray tube is operated at two different voltages and with different filter materials placed in front of the tube. The combination of different tube voltages and filter materials produces two distinct x-ray sources, where each source is optimal for unique groups of elements. However, as with the two isotope solution, this approach does not yield a second x-ray source that is selectable to not excite certain high concentration elements and yet optimally excites other elements typically at low concentrations.

U.S. Pat. No. 6,859,517, incorporated herein by this reference, discloses a dual source analyzer specifically for analyzing marine oils and fuels. This solution uses two radioisotope sources but two different samples are irradiated independently by the two x-ray sources. The subject invention is quite different in that a single sample is analyzed with both sources, and the sources are tuned for optimal analyses as described above for marine and other applications.

Therefore, although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments. Other embodiments will occur to those skilled in the art and are within the following claims.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

What is claimed is:

1. A dual source XRF system comprising:
   a first x-ray source for directing x-rays in a first energy band at a sample, the first x-ray source chosen to not excite at least one high concentration element in the sample;
   at least a second x-ray source for directing x-rays in a second energy band at the sample, the second x-ray source chosen to excite the high concentration element;

a monochromator in the optical path between the first and/or second x-ray source and the sample;

a detector responsive to x-rays emitted by the sample after irradiation by the first and second x-ray sources; and an analyzer, responsive to the detector and configured:
  to detect at least a low concentration element in the sample based on irradiation of the sample by the first x-ray source and to detect at least the high concentration element in the sample based on irradiation of the sample by the second x-ray source, and
  to determine the amount of the high concentration element and the low concentration element and to adjust the determination of the low concentration element in the sample based on the determined amount of the high concentration element in the sample.

2. A dual source XRF system comprising:
a first x-ray source for directing x-rays in a first energy band at a sample;
at least a second x-ray source for directing x-rays in a second energy band at the sample;
a detector responsive to x-rays emitted by the sample after irradiation by the first and second x-ray sources;
an analyzer, responsive to the detector and configured to detect at least a first substance in the sample based on irradiation of the sample by the first x-ray source and detect at least a second substance in the sample based on irradiation of the sample by the second x-ray source, the analyzer further configured to determine the amount of the first and second substances and adjust the determination of the second substance in the sample based on the determined amount of the first substance in the sample; and
a controller, responsive to the analyzer, and configured to energize the first and second x-ray sources either simultaneously or sequentially.

3. The system of claim 2 in which the second x-ray source is a molybdenum anode x-ray tube.

4. The system of claim 3 further including a monochromator in the optical path between the molybdenum anode x-ray tube and the sample.

5. The system of claim 4 in which the monochromator includes an optical element composed of doubly curved crystal or a highly oriented pyrolytic graphite.

6. The system of claim 4 in which the sample is fuel oil, the analyzer is configured to determine the amount of sulfur in the fuel oil sample based on irradiation of the fuel sample by the first x-ray source, and the analyzer is configured to determine the amount of catfines (Si and Al content) in the fuel oil sample based on irradiation of the fuel sample by the molybdenum anode x-ray tube.

7. The system of claim 6 in which the determination of the amount of aluminum in the fuel oil sample depends on the amount of sulfur in the sample and the analyzer is configured to adjust the determination depending on the determined amount of sulfur in the sample.

8. A dual source XRF system comprising:
a first x-ray source for directing x-rays in a first energy band at a sample;
at least a second x-ray source for directing x-rays in a second energy band at the sample;
a detector responsive to x-rays emitted by the sample; and
an analyzer, responsive to the detector and configured:
  to determine the amount of a first substance in the sample based on irradiation of the sample by the first x-ray source,
  to determine the amount of a second substance in the sample based on irradiation of the sample by the second x-ray source, and
  to adjust the determination of the second substance in the sample based on the determined amount of the first substance in the sample.

9. A method of analyzing a sample, the method comprising:
energizing a first x-ray source to direct x-rays in a first energy band at a sample;
energizing at least a second x-ray source to direct x-rays in a second energy band at the sample;
analyzing x-rays emitted by the sample;
detecting at least a first substance in the sample based on irradiation of the sample by the first x-ray source;
detecting at least a second substance in the sample based on irradiation of the sample by the second x-ray source; and
determining the amount of the first and second substances and adjusting the determination of the amount of the second substance in the sample based on the determined amount of the first substance in the sample.

10. The method of claim 9 in which the second x-ray source is a molybdenum anode x-ray tube.

11. The method of claim 10 further including the step of converting the output of the molybdenum x-ray tube to a monochromatic beam directed at the sample.

12. The method of claim 11 in which the sample is fuel oil, the amount of sulfur in the fuel is determined based on irradiation of the fuel sample by the first x-ray source and the amount of catfines in the fuel sample is determined based on irradiation of the fuel sample by the molybdenum anode x-ray tube.

13. The method of claim 12 in which the amount of aluminum in the fuel sample is determined depending on the amount of sulfur in the sample.

14. A method of analyzing a sample, the method comprising:
directing x-rays in a first energy band at a sample;
directing x-rays in a second energy band at the sample;
detecting x-rays emitted by the sample;
determining the amount of at least a first substance in the sample based on irradiation of the sample by the first x-ray source;
determining the amount of at least a second substance in the sample based on irradiation of the sample by the second x-ray source; and
adjusting the determination of the second substance in the sample based on the determined amount of the first substance in the sample.

15. A method comprising:
directing x-rays in a first energy band at a sample using a first x-ray source chosen to not excite at least one high concentration element in the sample;
directing x-rays in a second energy band at the sample using a second x-ray source chosen to excite the high concentration element;
monochromating the output of the first and/or second x-ray source;
analyzing x-rays emitted by the sample after irradiation by the first and second x-ray sources;

detecting at least a low concentration element in the sample based on irradiation of the sample by the first x-ray source;

detecting at least the high concentration element in the sample based on irradiation of the sample by the second x-ray source;

determining the amount of the high concentration element and the low concentration element; and adjusting the determination of the low concentration element in the sample based on the determined amount of the high concentration element in the sample.

* * * * *

UNITED STATES PATENT AND TRADEMARK OFFICE
Certificate

Patent No. 7,440,541 B2

Patented: October 21, 2008

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Bradley Hubbard-Nelson, Concord, MA (US); Peter John Hardman, Woburn, MA (US); and Don Sackett, Bedford, MA (US).

Signed and Sealed this Twenty-First Day of August 2012.

MINH-TOAN TON
*Supervisory Patent Examiner*
Art Unit 2882
Technology Center 2800